Figure 1:
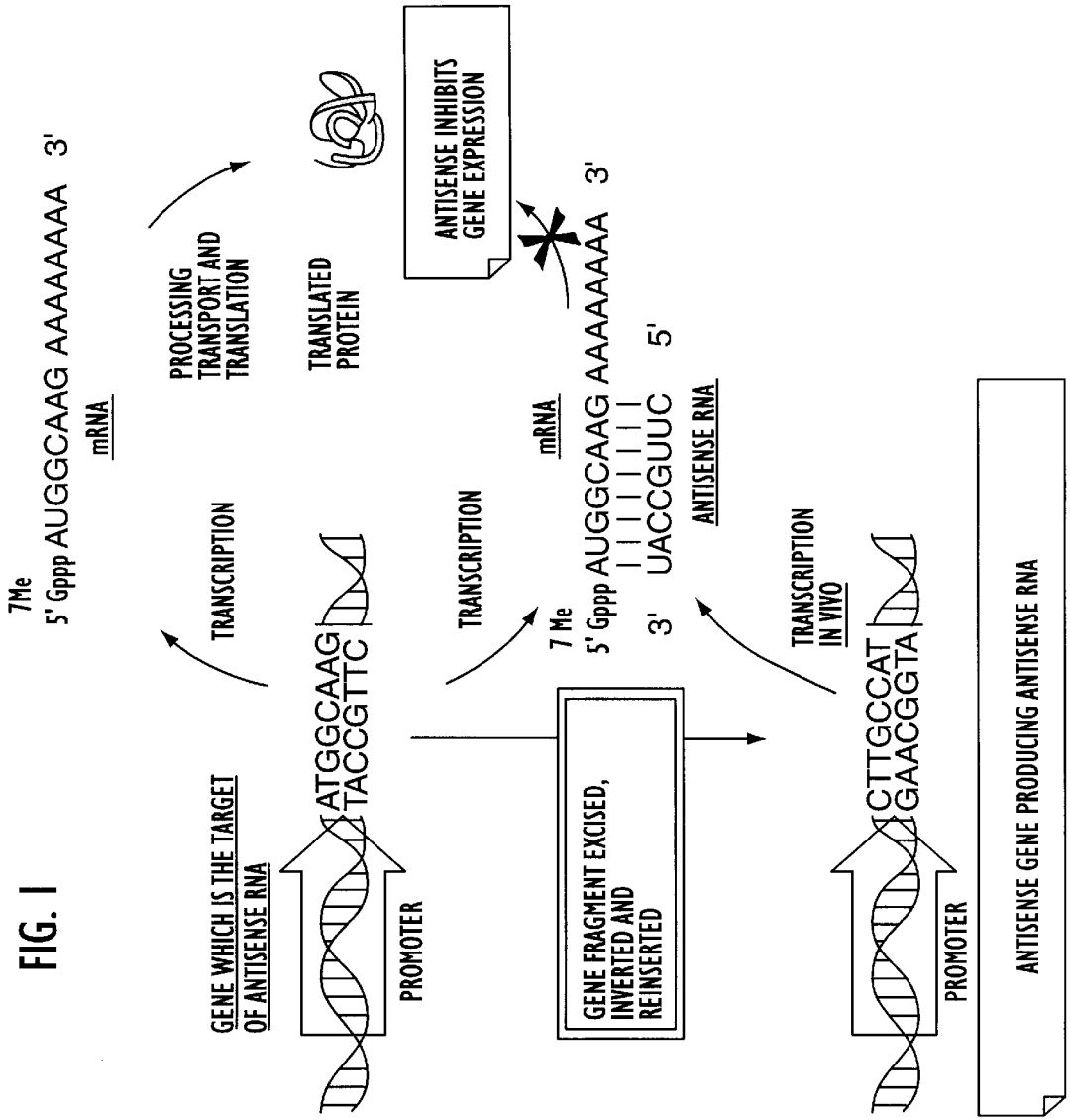

United States Patent [19]

Tallberg et al.

[11] Patent Number: 5,824,798

[45] Date of Patent: Oct. 20, 1998

[54] GENETICALLY ENGINEERED MODIFICATION OF POTATO TO OBTAIN AMYLOPECTIN-TYPE STARCH

[75] Inventors: Anneli Tallberg, Lund; Per Hofvander, Falsterbo; Per T. Persson; Olle Wikstrom, both of Kristianstad, all of Sweden

[73] Assignee: Amylogene HB, Svalöv, Sweden

[21] Appl. No.: 470,720

[22] Filed: Jun. 6, 1995

Related U.S. Application Data

[63] Continuation of Ser. No. 70,455, filed as PCT/SE91/00892 Dec. 20, 1991 published as WO92/11376 Jul. 9, 1992.

[30] Foreign Application Priority Data

Dec. 21, 1990 [SE] Sweden ................................ 9004096

[51] Int. Cl.$^6$ ................................ C07H 1/06; C07H 1/08
[52] U.S. Cl. ................................ 536/128; 536/45; 536/46; 536/55.3; 536/124; 536/127; 800/200; 800/205
[58] Field of Search ................................ 536/45, 46, 55.3, 536/124, 127, 128; 800/200, 205

[56] References Cited

U.S. PATENT DOCUMENTS

| | | | |
|---|---|---|---|
| 4,723,052 | 2/1988 | Cochran | 800/200 |
| 5,349,123 | 9/1994 | Shewmaker et al. | 800/205 |

FOREIGN PATENT DOCUMENTS

| | | |
|---|---|---|
| 0 335 451 | 10/1989 | European Pat. Off. |
| 0 368 506 | 5/1990 | European Pat. Off. |

OTHER PUBLICATIONS

"Inhibition of the Expression of the Gene for Granule–Bound Starch Synthase in Potato by Antisense Constructs", R.G.F. Visser et al., *Mol Gen Genet*, vol. 225, pp. 289–296, (1991).
"Molecular Cloning and Partial Characterization of the Gene for Granule–Bound Starch Synthase from a Wildtype and an Amylose–Free Potato (*Solanum Tuberosum L.*0", R.G.F. Visser et al., *Plant Science*, vol. 64, (1989), pp. 185–192.
"Structural and Functional Analysis of Two *Waxy* Gene Promoters from Potato", W. Rohde et al., *J. Genet. & Breed.* 44:311–315, (1990).

Isolation of an Amylose–Free Starch Mutant of the Potato (*Solanum Tuberosum L.*), J.H.M. Hovenkamp–Hermelink et al., *Theoretical and Applied Genetics*, (1987) 75, pp. 217–221.
"Sequence of the Structural Gene for Granule–Bound Starch Synthase of Potato (*Solanum Tuberosum L.*) and Evidence for a Single Point Deletion in the amf Allele", Feike R. van der Leij et al. *Mol Gen Genet*, vol. 228, pp. 240–248, (1991).
"Manipulation of the Starch Composition of (*Solanum Tuberosum L.*) Using *Agrobacterium Rhizogenes* Mediated Transformation", Ph D. Thesis of Richard G.F. Visser, Rijkduniversiteit Groningen, Feb. 27, 1989, pp. 1–141.
"Evidence that the waxy protein of pea (*Pisum sativum L.*) is Not the Major Starch–Granule–Bound Starch Synthase", Alison M. Smith, *Planta*, (1990), vol. 182, pp. 599–604.
"Characterization of cDNAs Encoding Two Isoforms of Granule–Bound Starch Synthase Which Show Different Expression in Developing Storage Organs of Pea and Potato", Ian Dry et al., *The Plant Journal*, (1992), 2(2), pp. 193–202.
Hovenkamp–Hermelink et al., Theoretical and Applied Genetics, vol. 75 pp. 217–221 (1987).
Hovenkamp–Hermelink et al., Potato Research, vol. 31, pp. 241–246, (1988).

*Primary Examiner*—James O. Wilson
*Attorney, Agent, or Firm*—Burns, Doane, Swecker & Mathis, L.L.P.

[57] ABSTRACT

Genetically engineered modification of potato for suppressing formation of amylose-type starch is described.

Three fragments for insertion in the antisense direction into the potato genome are also described. Moreover, antisense constructs, genes and vectors comprising said antisense fragments are described. Further a promoter for the gene coding for formation of granule-bound starch synthase and also the gene itself are described.

Also cells, plants, tubers, microtubers and seeds of potato comprising said antisense construct are described.

Finally, amylopectin-type starch, both native and derivatized, derived from the potato that is modified in a genetically engineered manner, as well as a method of suppressing amylose formation in potato are described.

8 Claims, 6 Drawing Sheets

GENETICALLY ENGINEERED MODIFICATION OF POTATO TO OBTAIN AMYLOPECTIN-TYPE STARCH

This application is a divisional of application Ser. No. 08/070,455, filed Nov. 24. 1993, which corresponds to PCT/SE91/00892, filed Dec. 20, 1991 published as WO92/11376 Jul. 9, 1992.

The present invention relates to genetically engineered modification of potato, resulting in the formation of practically solely amylopectin-type starch in the potato. The genetically engineered modification implies the insertion of gene fragments into potato, said gene fragments comprising parts of leader sequence, translation start, translation end and trailer sequence as well as coding and noncoding (i.e. exons and introns) parts of the gene for granule-bound starch synthase, inserted in the antisense direction.

BACKGROUND OF THE INVENTION

Starch in various forms is of great import in the food and paper industry. In future, starch will also be a great potential for producing polymers which are degradable in nature, e.g. for use as packing material. Many different starch products are known which are produced by derivatisation of native starch originating from, inter alia, maize and potato. Starch from potato and maize, respectively, is competing in most market areas.

In the potato tuber, starch is the greatest part of the solid matter. About ¼ to ⅕ of the starch in potato is amylose, while the remainder of the starch is amylopectin. These two components of the starch have different fields of application, and therefore the possibility of producing either pure amylose or pure amylopectin is most interesting. The two starch components can be produced from common starch, which requires a number of process steps and, consequently, is expensive and complicated.

It has now proved that by genetic engineering it is possible to modify potato so that the tubers merely produce mainly starch of one or the other type. As a result, a starch quality is obtained which can compete in the areas where potato starch is normally not used today. Starch from such potato which is modified in a genetically engineered manner has great potential as a food additive, since it has not been subjected to any chemical modification process.

Starch Synthesis

The synthesis of starch and the regulation thereof are presently being studied with great interest, both on the level of basic research and for industrial application. Although much is known about the assistance of certain enzymes in the transformation of saccharose into starch, the biosynthesis of starch has not yet been elucidated. By making researches above all into maize, it has, however, been possible to elucidate part of the ways of synthesis and the enzymes participating in these reactions. The most important starch-synthesising enzymes for producing the starch granules are the starch synthase and the branching enzyme. In maize, three forms of starch synthase have so far been demonstrated and studied, two of which are soluble and one is insolubly associated with the starch granules. Also the branching enzyme consists of three forms which are probably coded by three different genes (Mac Donald & Preiss, 1985; Preiss, 1988).

The Waxy Gene in Maize

The synthesis of the starch component amylose essentially occurs by the action of the starch synthase alpha-1,4-D-glucane-4-alpha-glucosyl transferase (EC 2.4.1.21) which is associated with the starch granules in the growth cell. The gene coding for this granule-bound enzyme is called "waxy" (=$wx^+$), while the enzyme is called "GBSS" (granule-bound starch synthase).

waxy locus in maize has been thoroughly characterised both genetically and biochemically. The waxy gene on chromosome 9 controls the production of amylose in endosperm, pollen and the embryo sac. The starch formed in endosperm in normal maize with the $wx^+$ allele consists to 25% of amylose and to 75% of amylopectin. A mutant form of maize has been found in which the endosperm contains a mutation located to the $wx^+$ gene, and therefore no functioning GBSS is synthesised. Endosperm from this mutant maize therefore contains merely amylopectin as the starch component. This so-called waxy mutant thus contains neither GBSS nor amylose (Echt & Schwartz, 1981).

The GBSS protein is coded by the $wx^+$ gene in the cell nucleus but is transported to and active in the amyloplast. The preprotein therefore consists of two components, viz. a 7 kD transit peptide which transfers the protein across the amyloplast membrane, and the actual protein which is 58 kD. The coding region of the $wx^+$ gene in maize is 3.7 kb long and comprises 14 exons and 13 introns. A number of the regulation signals in the promoter region are known, and two different polyadenylating sequences have been described (Klösgen et al, 1986; Schwartz-Sommer et al, 1984; Shure et al, 1983).

Amylose Enzyme in Potato

In potato, a 60 kD protein has been identified, which constitutes the main granule-bound protein. Since antibodies against this potato enzyme cross-react with GBSS from maize, it is assumed that it is the granule-bound synthase (Vos-Scheperkeuter et al, 1986). The gene for potato GBSS has, however, so far not been characterised to the same extent as the waxy gene in maize, either in respect of locating or structure.

Naturally occurring waxy mutants have been described for barley, rice and sorghum besides maize. In potato no natural mutant has been found, but a mutant has been produced by X-radiation of leaves from a monohaploid (n=12) plant (Visser et al, 1987). Starch isolated from tubers of this mutant contains neither the GBSS protein nor amylose. The mutant is conditioned by a simple recessive gene and is called amf. It may be compared to waxy mutants of other plant species since both the GBSS protein and amylose are lacking. The stability of the chromosome number, however, is weakened since this is quadrupled to the natural number (n=48), which can give negative effects on the potato plants (Jacobsen et al, 1990).

Inhibition of Amylose Production

The synthesis of amylose can be drastically reduced by inhibition of the granule-bound starch synthase, GBSS, which catalyses the formation of amylose. This inhibition results in the starch mainly being amylopectin.

Inhibition of the formation of enzyme can be accomplished in several ways, e.g. by:
- mutagen treatment which results in a modification of the gene sequence coding for the formation of the enzyme
- incorporation of a transposon in the gene sequence coding for the enzyme
- genetically engineered modification so that the gene coding for the enzyme is not expressed, e.g. antisense gene inhibition.

FIG. 1 illustrates a specific suppression of normal gene expression in that a complementary antisense nucleotide is allowed to hybridise with mRNA for a target gene. The antisense nucleotide thus is antisense RNA which is transcribed in vivo from a "reversed" gene sequence (Izant, 1989).

By using the antisense technique, various gene functions in plants have been inhibited. The antisense construct for chalcone synthase, polygalacturonase and phosphinotricin acetyltransferase has been used to inhibit the corresponding enzyme in the plant species petunia, tomato and tobacco.

Inhibition of Amylose in Potato

In potato, experiments have previously been made to inhibit the synthesis of the granule-bound starch synthase (GBSS protein) with an antisense construct corresponding to the gene coding for GBSS (this gene is hereinafter called the "GBSS gene"). Hergersberger (1988) describes a method by which a cDNA clone for the GBSS gene in potato has been isolated by means of a cDNA clone for the $wx^+$ gene in maize. An antisense construct based on the entire cDNA clone was transferred to leaf discs of potato by means of *Agrobacterium tumefaciens*. In microtubers induced in vitro from regenerated potato sprouts, a varying and very weak reduction of the amylose content was observed and shown in a diagram. A complete characterisation of the GBSS gene is not provided.

The gene for the GBSS protein in potato has been further characterised in that a genomic $wx^+$ clone was examined by restriction analysis. However, the DNA sequence of the clone has not been determined (Visser et al, 1989).

Further experiments with an antisense construct corresponding to the GBSS gene in potato have been reported. The antisense construct which is based on a cDNA clone together with the CaMV 35S promoter has been transformed by means of *Agrobacterium rhizogenes*. According to information, the transformation resulted in a lower amylose content in the potato, but no values have been accounted for (Flavell, 1990).

None of the methods used so far for genetically engineered modification of potato has resulted in potato with practically no amylose-type starch.

The object of the invention therefore is to provide a practically complete suppression of the formation of amylose in potato tubers.

SUMMARY OF THE INVENTION

According to the invention, the function of the GBSS gene and, thus, the amylose production in potato are inhibited by using completely new antisense constructs. For forming the antisense fragments according to the invention, the genomic GBSS gene is used as a basis in order to achieve an inhibition of GBSS and, consequently, of the amylose production, which is as effective as possible. The antisense constructs according to the invention comprise both coding and noncoding parts of the GBSS gene which correspond to sequences in the region comprising promoter as well as leader sequence, translation start, translation end and trailer sequence in the antisense direction. For a tissue-specific expression, i.e. the amylose production should be inhibited in the potato tubers only, use is made of promoters which are specifically active in the potato tuber. As a result, the starch composition in other parts of the plant is not affected, which otherwise would give negative side-effects.

The invention thus comprises a fragment which essentially has one of the nucleotide sequences stated in SEQ ID No. 1, SEQ ID No. 2 or SEQ ID No. 3. However, the sequences may deviate from those stated by one or more non-adjacent base pairs, without affecting the function of the fragments.

The invention also comprises a potato-tuber-specific promoter comprising 987 bp which belongs to the gene according to the invention, which codes for granule-bound starch synthase. Neither the promoter nor the corresponding gene has previously been characterised. The promoter sequence of 987 bp is stated in SEQ ID No. 4, while the gene sequence is stated in SEQ ID No. 5. Also the promoter and gene sequences may deviate from those stated by one or more non-adjacent base pairs, without affecting their function.

The invention also comprises vectors including the antisense fragments and the antisense constructs according to the invention.

In other aspects the invention comprises cells, plants, tubers, microtubers and seeds whose genome contains the fragments according to the invention inserted in the antisense direction.

In still further aspects, the invention comprises amylopectin-type starch, both native and derivatised.

Finally, the invention comprises a method of suppressing amylose formation in potato, whereby mainly amylopectin-type starch is formed in the potato.

Figure 2:
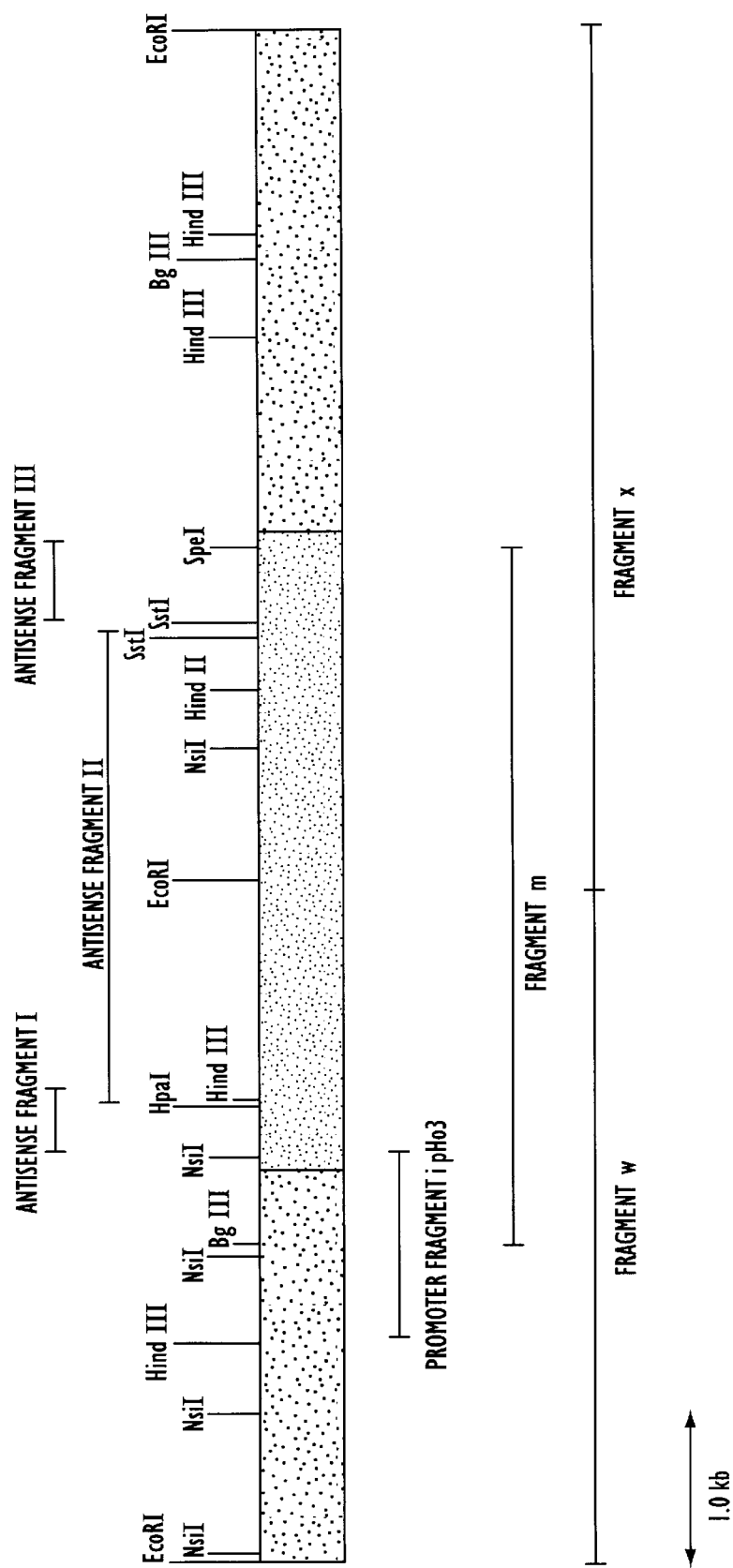
Figure 3:
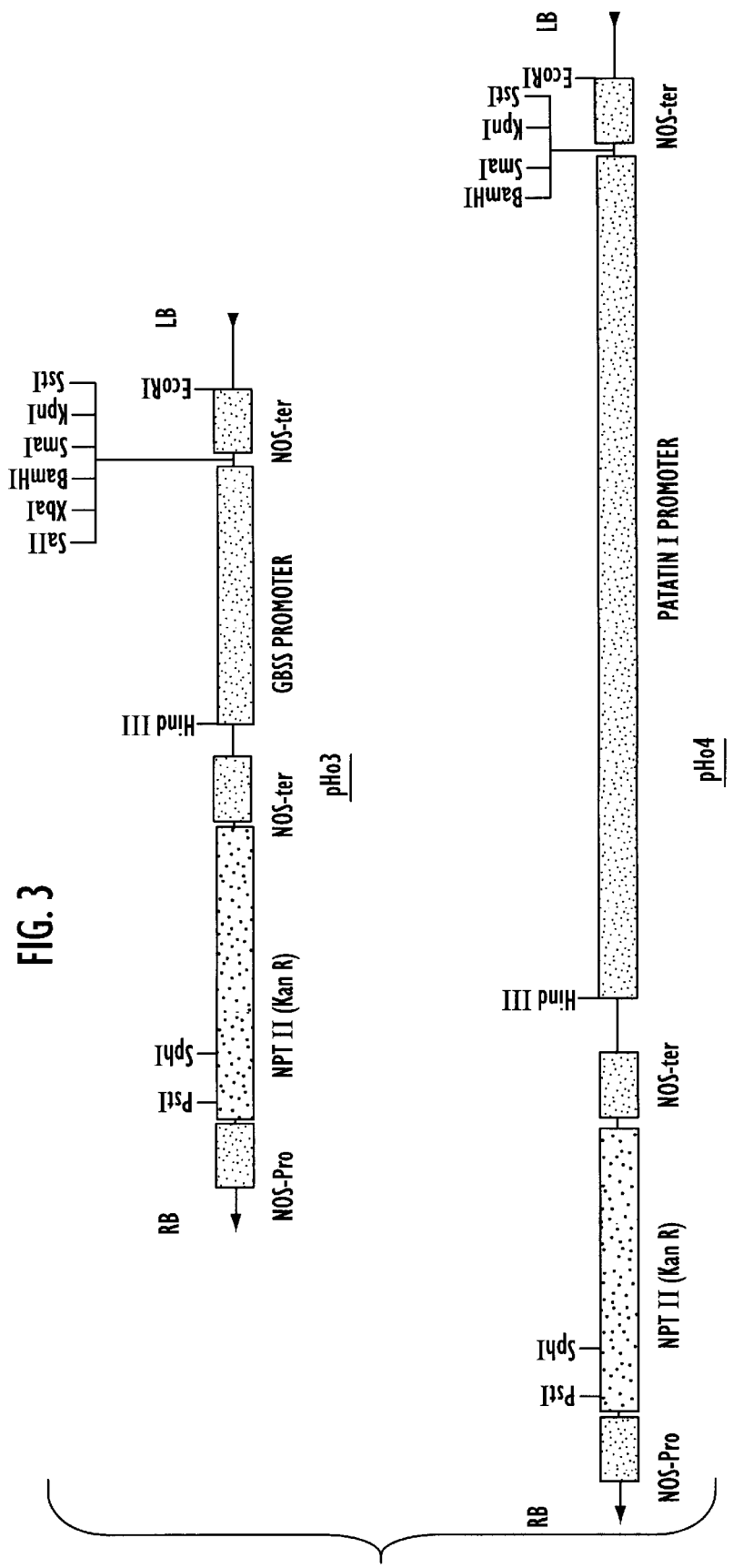
Figure 4:
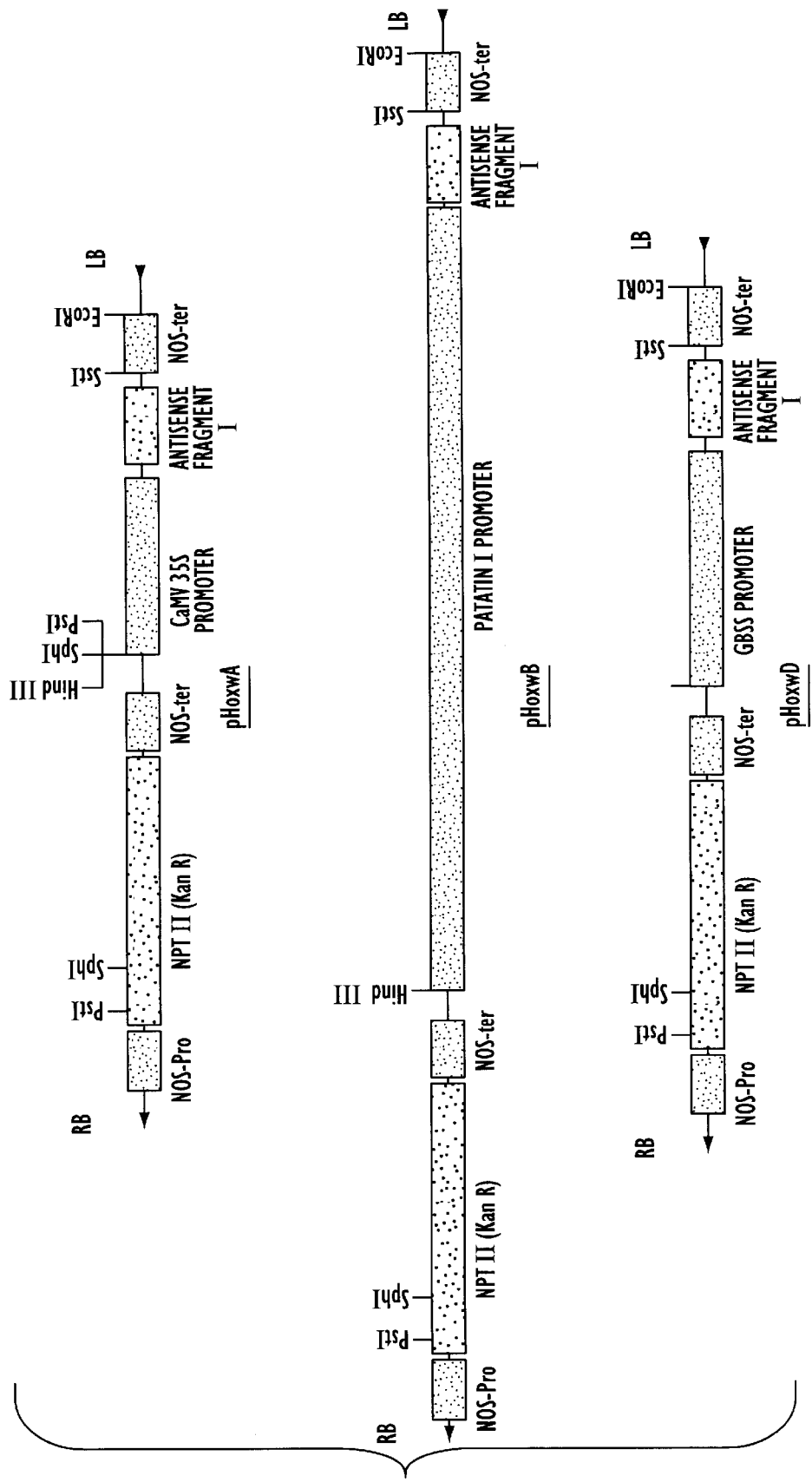
Figure 5:
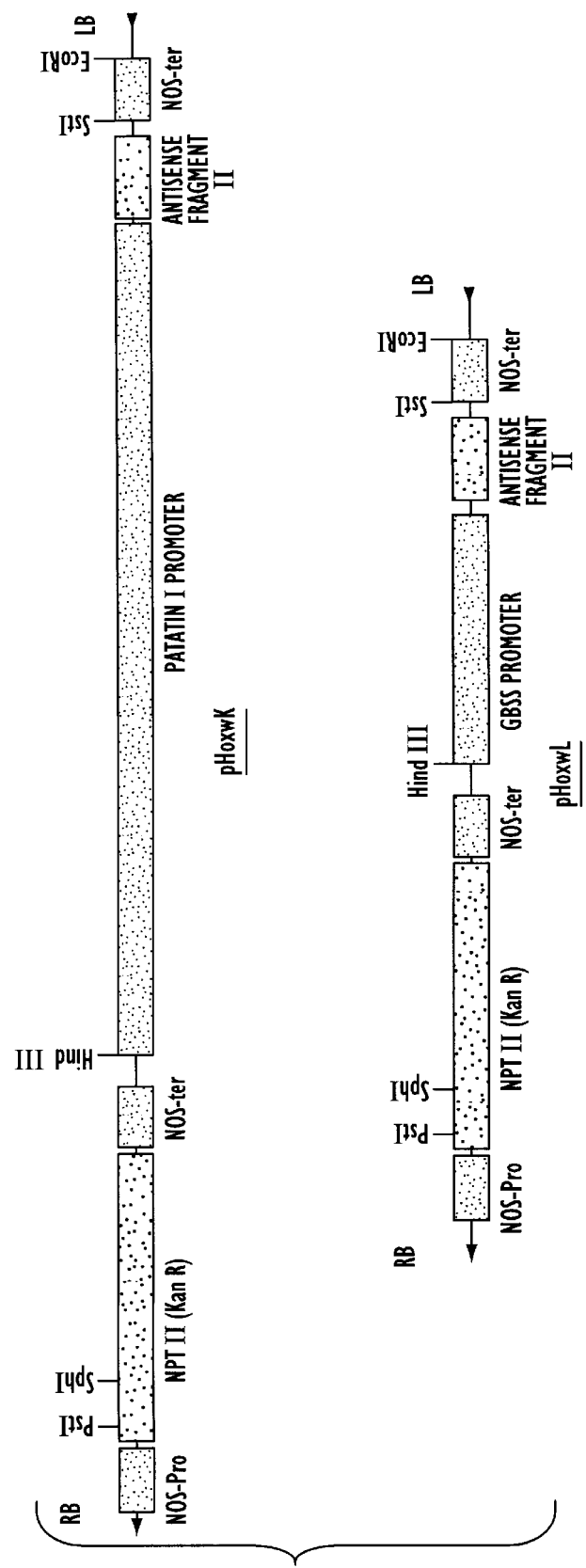
Figure 6:
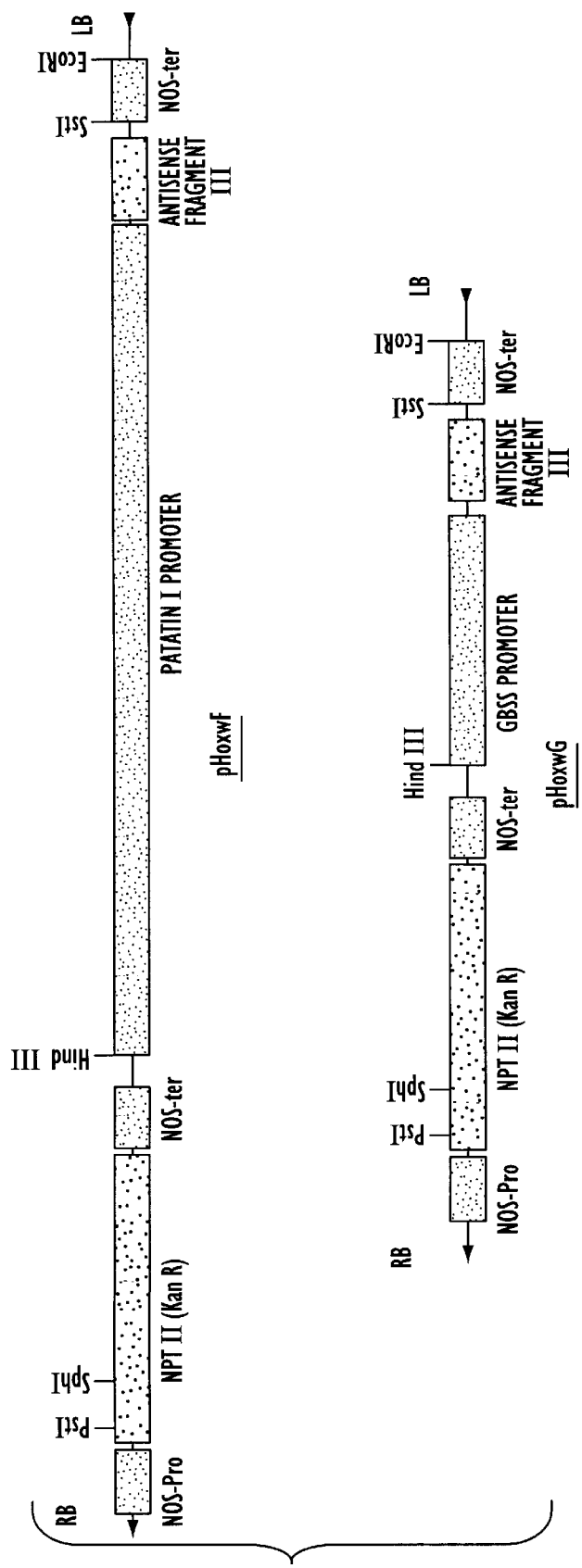

The invention will now be described in more detail with reference to the accompanying Figures in which FIG. 1 illustrates the principle of the antisense gene inhibition SEQ ID No. 21, FIG. 2 shows the result of restriction analysis of the potato GBSS gene, FIG. 3 shows two new binary vectors pHo3 and pHo4, FIG. 4 shows the antisense constructs pHoxwA, pHoxwB and pHoxwD, FIG. 5 shows the antisense constructs pHoxwF and pHoxwG, and FIG. 6 shows the antisense constructs pHoxwK and pHoxwL.

Moreover, the sequences of the different DNA fragments according to the invention are shown in SEQ ID Nos 1, 2, 3, 4 and 5. There may be deviations from these sequences in one or more non-adjacent base pairs.

MATERIALS

In the practical carrying out of the invention the following materials were used:

Bacterial strains: *E. coli* DH5alfa and DH5alfaF'IQ (BRL). *E. coli* JM105 (Pharmacia). *A. tumefaciens* LBA4404 (Clontech).

Vectors: M13mp18 and mp19 (Pharmacia). pBI101 and pBI121 (Clontech). pBI240.7 (M. W. Bevan). pUC plasmids (Pharmacia).

Enzymes: Restriction enzymes and EcoRI linker (BRL). UNION™ DNA Ligation Kit (Clontech). Sequenase™ DNA Sequencing Kit (USB). $T_4$-DNA ligase (Pharmacia).

The above-mentioned materials are used according to specifications stated by the manufacturers.

Genomic Library

A genomic library in EMBL3 has been produced by Clontech on the applicant's account, while using leaves of the potato Bintje as starting material.

Identification and Isolation of the GBSS Gene

The genomic library has been screened for the potato GBSS gene by means of cDNA clones for both the 5' and 3' end of the gene (said cDNA clones being obtained from M Hergersberger, Max Plank Institute in Cologne) according to a protocol from Clontech.

A full-length clone of the potato GBSS gene, wx311, has been identified and isolated from the genomic library. The start of the GBSS gene has been determined at an EcoRI fragment which is called fragment w (3.95 kb). The end of the GBSS gene has also been determined at an EcoRI fragment which is called fragment x (5.0 kb). A BglII-SpeI fragment which is called fragment m (3.9 kb) has also been isolated and shares sequences both from fragment w and from fragment x. The fragments w, m and x have been subcloned in pUC13 (Viera, 1982; Yanisch-Peron et al, 1985) and are called pSw, pSm and pSx, respectively (FIG. 2).

Characterisation of the GBSS Gene in Potato

The GBSS gene in potato has been characterised by restriction analysis and cDNA probes, where the 5' and 3' end of the GBSS gene has been determined more accurately (FIG. 2). Sequence determination according to Sanger et al, 1977 of the GBSS gene has been made on subclones from pSw and pSx in M13mp18 and mp19 as well as pUC19 starting around the 5' end (see SEQ ID No. 5).

The promoter region has been determined at a BglII-NsiI fragment (see SEQ ID No. 4). Transcription and translation start has been determined at an overlapping BglII-HindIII fragment. The terminator region has in turn been determined at a SpeI-HindIII fragment.

Antisense Constructs for the GBSS Gene in Potato

The GBSS gene fragments according to the invention (see SEQ ID Nos 1, 2 and 3, and FIG. 2) have been determined in the following manner.

The restriction of pSw with NsiI and HindIII gives fragment I (SEQ ID No. 1) which subcloned in pUC19 is called 19NH35. Further restriction of 19 NH35 with HpaI-SstI gives a fragment containing 342 bp of the GBSS gene according to the invention. This fragment comprises leader sequence, translation start and the first 125 bp of the coding region.

The restriction of pSm with HpaI and NsiI gives fragment II (SEQ ID No. 2) which subcloned in pJRD184 (Heusterspreute et al, 1987) is called pJRDmitt. Further restriction of pJRDmitt with HpaI-SstI gives a fragment containing 2549 bp of the GBSS gene according to the invention. This fragment comprises exons and introns from the middle of the gene.

The restriction of pSx with SstI and SpeI gives fragment III (SEQ ID No. 3) which subcloned in pbluescript (Melton et al, 1984) is called pBlue3'. Further restriction of pBlue3' with BamHI-SstI gives a fragment containing 492 bp of the GBSS gene according to the invention. This fragment comprises the last intron and exon, translation end and 278 bp of trailer sequence.

Antisense Constructs with Fragment I (FIG. 4): For the antisense construct pHoxwA, the HpaI-SstI fragment from 19NH35 has been inserted in the antisense direction into the binary vector pBI121 (Jefferson et al, 1987) cleaved with SmaI-SstI. The transcription of the antisense fragment is then initiated by the CaMV 35S promoter and is terminated by the NOS terminator (NOS =nopaline synthase).

For the antisense construct pHoxwB, the HpaI-SstI fragment from 19NH35 has been inserted in the antisense direction into the binary vector pHo4 (FIG. 3) cleaved with SmaI-SstI. The patatin I promoter which is tuber specific in potato comes from the vector pBI240.7 obtained from M. Bevan, Institute of Plant Science Research, Norwich. The transcription of the antisense fragment is then initiated by the patatin I promoter and is terminated by the NOS terminator.

For the antisense construct pHoxwD, the HpaI-SstI fragment from 19NH35 has been inserted in the antisense direction into the binary vector pHo3 (FIG. 3) cleaved with SmaI-SstI. pHo3 is a new binary vector which is constructed on the basis of pBI101. This vector which contains the promoter according to the invention (see SEQ ID No. 4) (GBSS promoter) of the now characterised potato GBSS gene according to the invention has been restriction-cleaved with SmaI and SstI, the HpaI-SstI fragment from 19NH35 being inserted in the antisense direction. The transcription of the antisense fragment is then initiated by its own GBSS promoter and is terminated by the NOS terminator. This means that the antisense fragment is transcribed only in the potato tuber, since the GBSS promoter like the patatin I promoter is tuber-specific.

Antisense Constructs with Fragment II (FIG. 5): For the antisense construct pHoxwF, the HpaI-SstI fragment from pJRDmitt has been inserted in the antisense direction into the binary vector pHo4 cleaved with SmaI-SstI. The transcription of the antisense fragment is then initiated by the patatin I promoter and terminated by the NOS terminator.

For the antisense construct pHoxwG, the HpaI-SstI fragment from pJRDmitt has been inserted in the antisense direction into the binary vector pHo3 cleaved with SmaI-SstI. The transcription of the antisense fragment is then initiated by its own GBSS promoter and is terminated by the NOS terminator.

Antisense Constructs with Fragment III (FIG. 6): For the antisense construct pHoxwK, the BamHI-SstI fragment from pBlue3' has been inserted in the antisense direction into the binary vector pHo4 cleaved with BamHI-SstI. The transcription of the antisense fragment is then initiated by the patatin I promoter and is terminated by the NOS terminator.

For the antisense construct pHoxwL, the BamHI-SstI fragment from pBlue3' has been inserted in the antisense direction into the binary vector pHo3 cleaved with BamHI-SstI. The transcription of the antisense fragment is then initiated by its own GBSS promoter and is terminated by the NOS terminator.

The formed antisense constructs (FIGS. 4, 5, 6) have been transformed to *Agrobacterium tumefaciens* strain LBA4404 by direct transformation with the "freeze-thawing" method (Hoekema et al, 1983; An et al, 1988).

Transformation

The antisense constructs are transferred to bacteria, suitably by the "freeze-thawing" method (An et al, 1988). The transfer of the recombinant bacterium to potato tissue occurs by incubation of the potato tissue with the recombinant bacterium in a suitable medium after some sort of damage has been inflicted upon the potato tissue. During the incubation, T-DNA from the bacterium enters the DNA of the host plant. After the incubation, the bacteria are killed and the potato tissue is transferred to a solid medium for callus induction and is incubated for growth of callus.

After passing through further suitable media, sprouts are formed which are cut away from the potato tissue.

Checks for testing the expression of the antisense constructs and the transfer thereof to the potato genome are carried out by e.g. southern and northern hybridisation (Maniatis et al (1982)). The number of copies of the antisense construct which has been transferred is determined by southern hybridisation.

The testing of the expression on protein level is suitably carried out on microtubers induced in vitro on the transformed sprouts, thus permitting the testing to be performed as quickly as possible.

Characterisation of the GBSS Protein

The effect of the antisense constructs on the function of the GBSS gene with respect to the activity of the GBSS protein is examined by extracting starch from the microtubers and analysing it regarding the presence of the GBSS protein. In electrophoresis on polyacrylamide gel (Hovenkamp-Hermelink et al, 1987), the GBSS protein forms a distinct band at 60 kD, when the GBSS gene functions. When the GBSS gene is not expressed, i.e. when the antisense GBSS gene is fully expressed, thereby inhibiting the formation of GBSS protein, no 60 kD band is demonstrated on the gel.

Characterisation of the Starch

The composition of the starch in microtubers is identical with that of ordinary potato tubers, and therefore the effect of the antisense constructs on the amylose production is examined in microtubers. The proportion of amylose to amylopectin can be determined by a spectrophoto-metric method (e.g. according to Hovenkamp-Hermelink et al, 1988).

Extraction of Amylopectin from Amylopectin Potato

Amylopectin is extracted from the so-called amylopectin potato (potato in which the formation of amylose has been suppressed by inserting the antisense constructs according to the invention) in a known manner.

Derivatisation of Amylopectin

Depending on the final use of the amylopectin, its physical and chemical qualities can be modified by derivatisation. By derivatisation is here meant chemical, physical and enzymatic treatment and combinations thereof (modified starches).

The chemical derivatisation, i.e. chemical modification of the amylopectin, can be carried out in different ways, for example by oxidation, acid hydrolysis, dextrinisation, different forms of etherification, such as cationisation, hydroxy propylation and hydroxy ethylation, different forms of esterification, for example by vinyl acetate, acetic anhydride, or by monophosphatising, diphosphatising and octenyl succination, and combinations thereof.

Physical modification of the amylopectin can be effected by e.g. cylinder-drying or extrusion.

In enzymatic derivatisation, degradation (reduction of the viscosity) and chemical modification of the amylopectin are effected by means of existing enzymatic systems.

The derivatisation is effected at different temperatures, according to the desired end product. The ordinary range of temperature which is used is 20°–45° C., but temperatures up to 180° C. are possible.

The invention will be described in more detail in the following Examples.

EXAMPLE 1

Production of microtubers with inserted antisense constructs according to the invention The antisense constructs (see FIGS. 4, 5 and 6) are transferred to *Agrobacterium tumefaciens* LBA 4404 by the "freeze-thawing" method (An et al, 1988). The transfer to potato tissue is carried out according to a modified protocol from Rocha-Sosa et al (1989).

Leaf discs from potato plants cultured in vitro are incubated in darkness on a liquid MS-medium (Murashige & Skoog; 1962) with 3% saccharose and 0.5% MES together with 100 $\mu$l of a suspension of recombinant Agrobacterium per 10 ml medium for two days. After these two days the bacteria are killed. The leaf discs are transferred to a solid medium for callus induction and incubated for 4–6 weeks, depending on the growth of callus. The solid medium is composed as follows:

MS+3% saccharose
2 mg/l zeatin riboside
0.02 mg/l "NAA"
0.02 mg/l "GA$_3$"
500 mg/l "Claforan"
50 mg/l kanamycin
0.25% "Gellan"

Subsequently the leaf discs are transferred to a medium having a different composition of hormones, comprising:

MS+3% saccharose
5 mg/l "NAA"
0.1 mg/l "BAP"
500 mg/l "Claforan"
50 mg/l kanamycin
0.25% "Gellan"

The leaf discs are stored on this medium for about 4 weeks, whereupon they are transferred to a medium in which the "Claforan" concentration has been reduced to 250 mg/l. If required, the leaf discs are then moved to a fresh medium every 4 or 5 weeks. After the formation of sprouts, these are cut away from the leaf discs and transferred to an identical medium.

The condition that the antisense construct has been transferred to the leaf discs is first checked by analysing leaf extracts from the regenerated sprouts in respect of glucuronidase activity by means of the substrates described by Jefferson et al (1987). The activity is demonstrated by visual assessment.

Further tests of the expression of the antisense constructs and the transfer thereof to the potato genome are carried out by southern and northern hybridisation according to Maniatis et al (1981). The number of copies of the antisense constructs that has been transferred is determined by southern hybridisation.

When it has been established that the antisense constructs have been transferred to and expressed in the potato genome, the testing of the expression on protein level begins. The testing is carried out on microtubers which have been induced in vitro on the transformed sprouts, thereby avoiding the necessity of waiting for the development of a complete potato plant with potato tubers.

Stem pieces of the potato sprouts are cut off at the nodes and placed on a modified MS medium. There they form microtubers after 2–3 weeks in incubation in darkness at 9° C. (Bourque et al, 1987). The medium is composed as follows:

MS+6% saccharose
2.5 mg/l kinetin
2.5 mg/l "Gellan"

The effect of the antisense constructs on the function of the GBSS gene in respect of the activity of the GBSS protein is analysed by means of electrophoresis on polyacrylamide gel (Hovenkamp-Hermelink et al, 1987). Starch is extracted from the microtubers and analysed regarding the presence of the GBSS protein. In a polyacrylamide gel, the GESS protein forms a distinct band at 60 kD, when the GESS gene functions. If the GBSS gene is not expressed, i.e. when the antisense GBSS gene is fully expressed so that the formation of GBSS protein is inhibited, no 60 kD band can be seen on the gel.

The composition of the starch, i.e. the proportion of amylose to amylopectin, is determined by a spectrophotometric method according to Hovenkamp-Hermelink et al (1988), the content of each starch component being determined on the basis of a standard graph.

EXAMPLE 2

Extraction of amylopectin from amylopectin potato.

Potato whose main starch component is amylopectin, below called amylopectin potato, modified in a genetically engineered manner according to the invention, is grated, thereby releasing the starch from the cell walls.

The cell walls (fibres) are separated from fruit juice and starch in centrifugal screens (centrisiler). The fruit juice is separated from the starch in two steps, viz. first in hydrocyclones and subsequently in specially designed band-type vacuum filters.

Then a finishing refining is carried out in hydrocyclones in which the remainder of the fruit juice and fibres are separated.

The product is dried in two steps, first by predrying on a vacuum filter and subsequently by final drying in a hot-air current.

EXAMPLE 3

Chemical derivatisation of amylopectin

Amylopectin is sludged in water to a concentration of 20–50%. The pH is adjusted to 10.0–12.0 and a quatenary ammonium compound is added in such a quantity that the end product obtains a degree of substitution of 0.004–0.2. The reaction temperature is set at 20°–45° C. When the reaction is completed, the pH is adjusted to 4–8, whereupon the product is washed and dried. In this manner the cationic starch derivative 2-hydroxy-3-trimethyl ammonium propyl ether is obtained.

EXAMPLE 4

Chemical derivatisation of amylopectin

Amylopectin is sludged in water to a water content of 10–25% by weight. The pH is adjusted to 10.0–12.0, and a quatenary ammonium compound is added in such a quantity that the end product obtains a degree of substitution of 0.004–0.2. The reaction temperature is set at 20°–45° C. When the reaction is completed, the pH is adjusted to 4–8. The end product is 2-hydroxy-3-trimethyl ammonium propyl ether.

EXAMPLE 5

Chemical derivatisation of amylopectin

Amylopectin is sludged in water to a concentration of 20–50% by weight. The pH is adjusted to 5.0–12.0, and sodium hypochlorite is added so that the end product obtains the desired viscosity. The reaction temperature is set at 20°–45° C. When the reaction is completed, the pH is adjusted to 4–8, whereupon the end product is washed and dried. In this manner, oxidised starch is obtained.

EXAMPLE 6

Physical derivatisation of amylopectin

Amylopectin is sludged in water to a concentration of 20–50% by weight, whereupon the sludge is applied to a heated cylinder where it is dried to a film.

EXAMPLE 7

Chemical and physical derivatisation of amylopectin

Amylopectin is treated according to the process described in one of Examples 3–5 for chemical modification and is then further treated according to Example 6 for physical derivatisation.

REFERENCES

Mac Donald, F. D. and Preiss, J., 1985, Plant. Physiol. 78:849–852

Preiss, J., 1988, In The Biochemistry of Plants 14 (Carbohydrates). Ed. J. Preiss, Academic Press; 181–254

Echt, C. S. and Schwarz, D., 1981, Genetics 99:275–284

Klösgen, R. B., Gierl, A., Schwarz-Sommer, Z. and Saedler, H., 1986, Mol. Gen. Genet. 203:237–244

Schwarz-Sommer, Z., Gierl, A., Klösgen, R. B., Wienand, U., Peterson, P. A. and Saedler, H., 1984, EMBO J. 3(5):1021–1028

Shure, M., Wessler, S. and Fedoroff, N., 1983, Cell 35:225–233

Jacobsen, E., Kriggsheld, H. T., Hovenkamp-Hermelink, J. H. M., Ponstein, A. S., Witholt, B. and Feenstra, W. J., 1990, Plant. Sci. 67:177–182

Visser, R. G. F., Hovenkamp-Hermelink, J. H. M., Ponstein, A. S., Vos-Scheperkeuter, G. H., Jacobsen, E., Feenstra, W. J. and Witholt, B., 1987, Proc. 4th European Congress on Biotechnology 1987, Vol. 2, Elsevier, Amsterdam; 432–435

Vos-Scheperkeuter, G. H., De Boer, W., Visser, R. G. F., Feenstra, W. J. and Witholt, B., 1986, Plant. Physiol. 82:411–416

Cornelissen, M., 1989, Nucleic Acids Res. 17(18) :7203–7209

Izant, J. G., 1989, Cell Motility and Cytosceleton 14:81–91

Sheehy; R. E., Kramer, M., Hiatt, W. R., 1988, Proc. Natl. Acad. Sci. USA, 85(23):8805–8809

Van der Krol, A. R., Mur, L. A., de Lange, P., Gerats, A. G. M., Mol, J. N. M. and Stuitje, A. R., 1960, Mol. Gen. Genet. 220:204–212

Flavell, R. B., 1990, AgBiotech. News and Information 2(5):629–630

Hergersberger, M., 1988, Molekulare Analyse des waxy Gens aus Solanum tuberosum und Expression von waxy antisense RNA in transgenen Kartoffeln. Thesis for a doctorate from the University in Cologne Visser, R. G. F., Hergersberger, M., van der Leij, F. R., Jacobsen, E., Witholt, B. and Feenstra, W. J., 1989, Plant. Sci. 64:185–192 An, G., Ebert, P. R., Mitra, A. and Ha, S. B., 1987, Plant Mol. Biol. Manual A3:1–19

Hoekema, A., Hirsch, P. R., Hooykaas, P. J. J. and Schilperoort, R. A., 1983, Nature 303:179–180

Jefferson, R. A., Kavanagh, T. A. and Bevan, M. W., 1987, EMBO J. 6:3201–3207

Sanger, F., Nicklen, S. and Coulson, A. R., 1977, Proc. Natl. Acad. Sci. USA 74:5463–5467

Viera, J. and Messing, J., 1982, Gene 19:259–268

Yanisch-Perron, C., Viera, J. and Messing, J., 1985, Gene 33:103–119

Heusterspreute et al (1987) Gene 53:294–300

Melton, D. A. et al (1984), Nucleic Acids Res. 12:7035–7056 (the plasmide is sold by Stratagene)

Murashige, T. and Skoog, F., 1962, Physiol. Plant 15:473–497.

Rocha-Sosa, M., Sonnewald, U., Frommer, W., Stratmann, M., Shell, J. and Willmitzer, L., 1989, EMBO J., 8(1):23–29

Jefferson, R. A., Kavanagh, R. A. and Bevan, M. W., 1987, EMBO J. 6:3901–3907

Maniatis, T., Fritsch, E. F. and Sambrook, J., 1982, Molecular Cloning, A Laboratory Handbook, Cold Spring Harbor Laboratory Press, Cold Spring Harbor Bourque, J. E., Miller, J. C. and Park, W. D., 1987, In Vitro Cellular & Development Biology 23(5):381–386

Hovenkamp-Hermelink, J. H. M., Jacobsen, E., Ponstein, A. S., Visser, R. G. F., Vos-Scheperkeuter, G. H., Bijmolt, E. W., de Vries, J. N., Witholt, B. J. & Feenstra, W. J., 1987, Theor. Appl. Genet. 75:217–221

Hovenkamp-Hermelink, J. H. M., de Vries, J. N., Adamse, P., Jacobsen, E., Witholt, B. and Feenstra, W. J., 1988, Potato Research 31:241–246

Modified starches: Properties and use D. B. Wurzburg

Bevan, M. W., 1984. Nucleic Acids Res. 12:8711–8721.

---

We claim:

1. A process for producing an amylopectin-type starch comprising:
  obtaining a potato tissue which has been transformed by introducing into the genome of the potato tissue a gene construct comprising a promoter and a fragment of the potato gene which codes for the formation of granule-bound starch synthase inserted in the anti-sense direction, wherein said fragment essentially has a nucleotide sequence which is selected from the group consisting of SEQ ID No. 1, SEQ ID No.2 and SEQ ID No. 3;
  growing the transformed potato tissue to produce a potato plant containing potato tubers;
  producing at least one potato from said potato tubers; and
  separating starch from said potato, wherein said starch is an amylopectin-type starch which is essentially free of amylose.

2. The process for producing an amylopectin-type starch according to claim 1, wherein said fragment has a nucleotide sequence of SEQ ID No. 1.

3. The process for producing an amylopectin-type starch according to claim 1, wherein said fragment has a nucleotide sequence of SEQ ID No. 2.

4. The process for producing an amylopectin-type starch according to claim 1, wherein said fragment has a nucleotide sequence of SEQ ID No. 3.

5. The process for producing an amylopectin-type starch according to claim 1, wherein said promoter comprises a CAMV 35S promoter.

6. The process for producing an amylopectin-type starch according to claim 1, wherein said promoter comprises a patatin I promoter.

7. The process for producing an amylopectin-type starch according to claim 1, wherein said promoter comprises a GBSS promoter.

8. The process for producing an amylopectin-type starch according to claim 7, wherein said GBSS promoter has the nucleotide sequence of SEQ ID No. 4.

\* \* \* \* \*

UNITED STATES PATENT AND TRADEMARK OFFICE
CERTIFICATE OF CORRRECTION

PATENT NO. : 5,824,798
DATED : October 20, 1998
INVENTOR(S) : Anneli Tallberg, et al It is certified that error appears in the above-identified patent and that said Letters Patent is hereby corrected as shown below:

On the title page, item [56], insert:

OTHER DOCUMENTS

| | |
|---|---|
| | M. Hergersberg, "A Molecular Analysis Of The Waxy Gene From Solanum Tuberosum And Expression Of Waxy Antisense RNA In Transgenic Potatoes," Translation of Dissertation pp. 25-64, and English translation. |

Signed and Sealed this

Thirteenth Day of April, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 342 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 217..342

( x i ) SEQUENCE DESCRIPTION: SEQ ID NO:1:

```
TGCATGTTTC  CCTACATTCT  ATTTAGAATC  GTGTTGTGGT  GTATAAACGT  TGTTTCATAT          60

CTCATCTCAT  CTATTCTGAT  TTTGATTCTC  TTGCCTACTG  TAATCGGTGA  TAAATGTGAA         120

TGCTTCCTTT  CTTCTCAGAA  ATCAATTTCT  GTTTTGTTTT  TGTTCATCTG  TAGCTTATTC         180

TCTGGTAGAT  TCCCCTTTTT  GTAGACCACA  CATCAC  ATG  GCA  AGC  ATC  ACA  GCT       234
                                            Met  Ala  Ser  Ile  Thr  Ala
                                             1                    5

TCA  CAC  CAC  TTT  GTG  TCA  AGA  AGC  CAA  ACT  TCA  CTA  GAC  ACC  AAA  TCA  282
Ser  His  His  Phe  Val  Ser  Arg  Ser  Gln  Thr  Ser  Leu  Asp  Thr  Lys  Ser
               10                       15                        20

ACC  TTG  TCA  CAG  ATA  GGA  CTC  AGG  AAC  CAT  ACT  CTG  ACT  CAC  AAT  GGT  330
Thr  Leu  Ser  Gln  Ile  Gly  Leu  Arg  Asn  His  Thr  Leu  Thr  His  Asn  Gly
               25                       30                        35

TTA  AGG  GCT  GTT                                                              342
Leu  Arg  Ala  Val
               40
```

( 2 ) INFORMATION FOR SEQ ID NO:2:

( i ) SEQUENCE CHARACTERISTICS:
        ( A ) LENGTH: 2549 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:2:

| | | | | | | |
|---|---|---|---|---|---|---|
| AACAAGCTTG | ATGGGCTCCA | ATCAACAACT | AATACTAAGG | TAACACCCAA | GATGGCATCC | 60 |
| AGAACTGAGA | CCAAGAGACC | TGGATGCTCA | GCTACCATTG | TTTGTGGAAA | GGGAATGAAC | 120 |
| TTGATCTTTG | TGGGTACTGA | GGTTGGTCCT | TGGAGCAAAA | CTGGTGGACT | AGGTGATGTT | 180 |
| CTTGGTGGAC | TACCACCAGC | CCTTGCAGTA | AGTCTTTCTT | TCATTTGGTT | ACCTACTCAT | 240 |
| TCATTACTTA | TTTTGTTTAG | TTAGTTTCTA | CTGCATCAGT | CTTTTTATCA | TTTAGGCCCG | 300 |
| CGGACATCGG | GTAATGACAA | TATCCCCCCG | TTATGACCAA | TACAAGATG | CTTGGGATAC | 360 |
| TGGCGTTGCG | GTTGAGGTAC | ATCTTCCTAT | ATTGATACGG | TACAATATTG | TTCTCTTACA | 420 |
| TTTCCTGATT | CAAGAATGTG | ATCATCTGCA | GGTCAAAGTT | GGAGACAGCA | TTGAAATTGT | 480 |
| TCGTTTCTTT | CACTGCTATA | AACGTGGGGT | TGATCGTGTT | TTTGTTGACC | ACCCAATGTT | 540 |
| CTTGGAGAAA | GTAAGCATAT | TATGATTATG | AATCCGTCCT | GAGGGATACG | CAGAACAGGT | 600 |
| CATTTTGAGT | ATCTTTTAAC | TCTACTGGTG | CTTTTACTCT | TTTAAGGTTT | GGGGCAAAAC | 660 |
| TGGTTCAAAA | ATCTATGGCC | CCAAAGCTGG | ACTAGATTAT | CTGGACAATG | AACTTAGGTT | 720 |
| CAGCTTGTTG | TGTCAAGTAA | GTTAGTTACT | CTTGATTTTT | ATGTGGCATT | TTACTCTTTT | 780 |
| GTCTTTAATC | GTTTTTTTAA | CCTTGTTTTC | TCAGGCAGCC | CTAGAGGCAC | CTAAAGTTTT | 840 |
| GAATTTGAAC | AGTAGCAACT | ACTTCTCAGG | ACCATATGGT | AATTAACACA | TCCTAGTTTC | 900 |
| AGAAAACTCC | TTACTATATC | ATTGTAGGTA | ATCATCTTTA | TTTTGCCTAT | TCCTGCAGGA | 960 |
| GAGGATGTTC | TCTTCATTGC | CAATGATTGG | CACACAGCTC | TCATTCCTTG | CTACTTGAAG | 1020 |
| TCAATGTACC | AGTCCAGAGG | AATCTACTTG | AATGCCAAGG | TAAAATTTCT | TTGTATTCAC | 1080 |
| TCGATTGCAC | GTTACCCTGC | AAATCAGTAA | GGTTGTATTA | ATATATGATA | AATTTCACAT | 1140 |
| TGCCTCCAGG | TTGCTTTCTG | CATCCATAAC | ATTGCCTACC | AAGGTCGATT | TTCTTTCTCT | 1200 |
| GACTTCCCTC | TTCTCAATCT | TCCTGATGAA | TTCAGGGGTT | CTTTTGATTT | CATTGATGGG | 1260 |
| TATGTATTTA | TGCTTGAAAT | CAGACCTCCA | ACTTTTGAAG | CTCTTTTGAT | GCTAGTAAAT | 1320 |
| TGAGTTTTTA | AAATTTTGCA | GATATGAGAA | GCCTGTTAAG | GGTAGGAAAA | TCAACTGGAT | 1380 |
| GAAGGCTGGG | ATATTAGAAT | CACATAGGGT | GGTTACAGTG | AGCCCATACT | ATGCCCAAGA | 1440 |
| ACTTGTCTCT | GCTGTTGACA | AGGGAGTTGA | ATTGGACAGT | GTCCTTCGTA | AGACTTGCAT | 1500 |
| AACTGGGATT | GTGAATGGCA | TGGATACACA | AGAGTGGAAC | CCAGCGACTG | ACAAATACAC | 1560 |
| AGATGTCAAA | TACGATATAA | CCACTGTAAG | ATAAGATTTT | TCCGACTCCA | GTATATACTA | 1620 |
| AATTATTTTG | TATGTTTATG | AAATTAAAGA | GTTCTTGCTA | ATCAAAATCT | CTATACAGGT | 1680 |
| CATGGACGCA | AAACCTTTAC | TAAAGGAGGC | TCTTCAAGCA | GCAGTTGGCT | TGCCTGTTGA | 1740 |
| CAAGAAGATC | CCTTTGATTG | GCTTCATCGG | CAGACTTGAG | GAGCAGAAAG | GTTCAGATAT | 1800 |
| TCTTGTTGCT | GCAATTCACA | AGTTCATCGG | ATTGGATGTT | CAAATTGTAG | TCCTTGTAAG | 1860 |
| TACCAAATGG | ACTCATGGTA | TCTCTCTTGT | TGAGTTTACT | TGTGCCGAAA | CTGAAATTGA | 1920 |
| CCTGCTACTC | ATCCTATGCA | TCAGGGAACT | GGCAAAAAGG | AGTTTGAGCA | GGAGATTGAA | 1980 |
| CAGCTCGAAG | TGTTGTACCC | TAACAAAGCT | AAAGGAGTGG | CAAAATTCAA | TGTCCCTTTG | 2040 |
| GCTCACATGA | TCACTGCTGG | TGCTGATTTT | ATGTTGGTTC | CAAGCAGATT | TGAACCTTGT | 2100 |
| GGTCTCATTC | AGTTACATGC | TATGCGATAT | GGAACAGTAA | GAACCAGAAG | AGCTTGTACC | 2160 |
| TTTTTACTGA | GTTTTTAAAA | AAAGAATCAT | AAGACCTTGT | TTTCCATCTA | AAGTTTAATA | 2220 |
| ACCAACTAAA | TGTTACTGCA | GCAAGCTTTT | CATTTCTGAA | AATTGGTTAT | CTGATTTTAA | 2280 |

-continued

| | | | | | |
|---|---|---|---|---|---|
| CGTAATCACA | TGTGAGTCAG | GTACCAATCT | GTGCATCGAC | TGGTGGACTT | GTTGACACTG | 2340 |
| TGAAAGAAGG | CTATACTGGA | TTCCATATGG | GAGCCTTCAA | TGTTGAAGTA | TGTGATTTTA | 2400 |
| CATCAATTGT | GTACTTGTAC | ATGGTCCATT | CTCGTCTTGA | TATACCCCTT | GTTGCATAAA | 2460 |
| CATTAACTTA | TTGCTTCTTG | AATTTGGTTA | GTGCGATGTT | GTTGACCCAG | CTGATGTGCT | 2520 |
| TAAGATAGTA | ACAACAGTTG | CTAGAGCTC | | | | 2549 |

( 2 ) INFORMATION FOR SEQ ID NO:3:

( i ) SEQUENCE CHARACTERISTICS:
        ( A ) LENGTH: 492 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..15

( i x ) FEATURE:
        ( A ) NAME/KEY: CDS
        ( B ) LOCATION: 101..218

( x i ) SEQUENCE DESCRIPTION: SEQ ID NO:3:

```
GAG  CTC  TCC  TGG  AAG  GTAAGTGTGA  ATTTGATAAT  TTGCGTAGGT  ACTTCAGTTT         55
Glu  Leu  Ser  Trp  Lys
 1                    5
GTTGTTCTCG  TCAGCACTGA  TGGATTCCAA  CTGGTGTTCT  TGCAG  GAA  CCT  GCC           109
                                                       Glu  Pro  Ala
                                                        1
AAG  AAA  TGG  GAG  ACA  TTG  CTA  TTG  GGC  TTA  GGA  GCT  TCT  GGC  AGT  GAA  157
Lys  Lys  Trp  Glu  Thr  Leu  Leu  Leu  Gly  Leu  Gly  Ala  Ser  Gly  Ser  Glu
 5                         10                          15
CCC  GGT  GTT  GAA  GGG  GAA  GAA  ATC  GCT  CCA  CTT  GCC  AAG  GAA  AAT  GTA  205
Pro  Gly  Val  Glu  Gly  Glu  Glu  Ile  Ala  Pro  Leu  Ala  Lys  Glu  Asn  Val
 20                        25                          30                   35
GCC  ACT  CCT  TAAATGAGCT  TTGGTTATCC  TTGTTTCAAC  AATAAGATCA               254
Ala  Thr  Pro  *
```

| | | | | | |
|---|---|---|---|---|---|
| TTAAGCAAAC | GTATTTACTA | GCGAACTATG | TAGAACCCTA | TTATGGGGTC | TCAATCATCT | 314 |
| ACAAAATGAT | TGGTTTTTGC | TGGGGAGCAG | CAGCATATAA | GGCTGTAAAA | TCCTGGTTAA | 374 |
| TGTTTTTGTA | GGTAAGGGCT | ATTTAAGGTG | GTGTGGATCA | AAGTCAATAG | AAAATAGTTA | 434 |
| TTACTAACGT | TTGCAACTAA | ATACTTAGTA | ATGTAGCATA | AATAATACTA | GAACTAGT | 492 |

( 2 ) INFORMATION FOR SEQ ID NO:4:

( i ) SEQUENCE CHARACTERISTICS:
        ( A ) LENGTH: 987 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| AAGCTTTAAC | GAGATAGAAA | ATTATGTTAC | TCCGTTTTGT | TCATTACTTA | ACAAATGCAA | 60 |
| CAGTATCTTG | TACCAAATCC | TTTCTCTCTT | TTCAAACTTT | TCTATTTGGC | TGTTGACGGA | 120 |
| GTAATCAGGA | TACAAACCAC | AAGTATTTAA | TTGACTCCTC | CGCCAGATAT | TATGATTTAT | 180 |
| GAATCCTCGA | AAAGCCTATC | CATTAAGTCC | TCATCTATGG | ATATACTTGA | CAGTATCTTC | 240 |
| CTGTTTGGGT | ATTTTTTTTT | CCTGCCAAGT | GGAACGGAGA | CATGTTATGA | TGTATACGGG | 300 |

-continued

```
AAGCTCGTTA  AAAAAAAATA  CAATAGGAAG  AAATGTAACA  AACATTGAAT  GTTGTTTTTA     360
ACCATCCTTC  CTTTAGCAGT  GTATCAATTT  TGTAATAGAA  CCATGCATCT  CAATCTTAAT     420
ACTAAAATGC  AACTTAATAT  AGGCTAAACC  AAGATAAAGT  AATGTATTCA  ACCTTTAGAA     480
TTGTGCATTC  ATAATTAGAT  CTTGTTTGTC  GTAAAAATT   AGAAATATA   TTTACAGTAA     540
TTTGGAATAC  AAAGCTAAGG  GGGAAGTAAC  TAATATTCTA  GTGGAGGGAG  GGACCAGTAC     600
CAGTACCTAG  ATATTATTTT  TAATTACTAT  AATAATAATT  TAATTAACAC  GAGACATAGG     660
AATGTCAAGT  GGTAGCGTAG  GAGGGAGTTG  GTTTAGTTTT  TTAGATACTA  GGAGACAGAA     720
CCGGACGGCC  CATTGCAAGG  CCAAGTTGAA  GTCCAGCCGT  GAATCAACAA  AGAGAGGGCC     780
CATAATACTG  TCGATGAGCA  TTTCCCTATA  ATACAGTGTC  CACAGTTGCC  TTCTGCTAAG     840
GGATAGCCAC  CCGCTATTCT  CTTGACACGT  GTCACTGAAA  CCTGCTACAA  ATAAGGCAGG     900
CACCTCCTCA  TTCTCACTCA  CTCACTCACA  CAGCTCAACA  AGTGGTAACT  TTTACTCATC     960
TCCTCCAATT  ATTTCTGATT  TCATGCA                                           987
```

( 2 ) INFORMATION FOR SEQ ID NO:5:

( i ) SEQUENCE CHARACTERISTICS:
      ( A ) LENGTH: 4964 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

```
AAGCTTTAAC  GAGATAGAAA  ATTATGTTAC  TCCGTTTTGT  TCATTACTTA  ACAAATGCAA      60
CAGTATCTTG  TACCAAATCC  TTTCTCTCTT  TTCAAACTTT  TCTATTTGGC  TGTTGACGGA     120
GTAATCAGGA  TACAAACCAC  AAGTATTTAA  TTGACTCCTC  CGCCAGATAT  TATGATTTAT     180
GAATCCTCGA  AAAGCCTATC  CATTAAGTCC  TCATCTATGG  ATATACTTGA  CAGTATCTTC     240
CTGTTTGGGT  ATTTTTTTT   CCTGCCAAGT  GGAACGGAGA  CATGTTATGA  TGTATACGGG     300
AAGCTCGTTA  AAAAAAAATA  CAATAGGAAG  AAATGTAACA  AACATTGAAT  GTTGTTTTTA     360
ACCATCCTTC  CTTTAGCAGT  GTATCAATTT  TGTAATAGAA  CCATGCATCT  CAATCTTAAT     420
ACTAAAATGC  AACTTAATAT  AGGCTAAACC  AAGATAAAGT  AATGTATTCA  ACCTTTAGAA     480
TTGTGCATTC  ATAATTAGAT  CTTGTTTGTC  GTAAAAATT   AGAAATATA   TTTACAGTAA     540
TTTGGAATAC  AAAGCTAAGG  GGGAAGTAAC  TAATATTCTA  GTGGAGGGAG  GGACCAGTAC     600
CAGTACCTAG  ATATTATTTT  TAATTACTAT  AATAATAATT  TAATTAACAC  GAGACATAGG     660
AATGTCAAGT  GGTAGCGTAG  GAGGGAGTTG  GTTTAGTTTT  TTAGATACTA  GGAGACAGAA     720
CCGGACGGCC  CATTGCAAGG  CCAAGTTGAA  GTCCAGCCGT  GAATCAACAA  AGAGAGGGCC     780
CATAATACTG  TCGATGAGCA  TTTCCCTATA  ATACAGTGTC  CACAGTTGCC  TTCTGCTAAG     840
GGATAGCCAC  CCGCTATTCT  CTTGACACGT  GTCACTGAAA  CCTGCTACAA  ATAAGGCAGG     900
CACCTCCTCA  TTCTCACTCA  CTCACTCACA  CAGCTCAACA  AGTGGTAACT  TTTACTCATC     960
TCCTCCAATT  ATTTCTGATT  TCATGCATGT  TTCCCTACAT  TCTATTATGA  ATCGTGTTGT    1020
GGTGTATAAA  CGTTGTTTCA  TATCTCATCT  CATCTATTCT  GATTTGATT   CTCTTGCCTA    1080
CTGTAATCGG  TGATAAATGT  GAATGCTTCC  TTTCTTCTCA  GAAATCAATT  TCTGTTTTGT    1140
TTTTGTTCAT  CTGTAGCTTA  TTCTCTGGTA  GATTCCCCTT  TTTGTAGACC  ACACATCACA    1200
TGGCAAGCAT  CACAGCTTCA  CACCACTTTG  TGTCAAGAAG  CCAAACTTCA  CTAGACACCA    1260
```

-continued

| | | | | | |
|---|---|---|---|---|---|
| AATCAACCTT | GTCACAGATA | GGACTCAGGA | ACCATACTCT | GACTCACAAT | GGTTTAAGGG | 1320
| CTGTTAACAA | GCTTGATGGG | CTCCAATCAA | CAACTAATAC | TAAGGTAACA | CCCAAGATGG | 1380
| CATCCAGAAC | TGAGACCAAG | AGACCTGGAT | GCTCAGCTAC | CATTGTTTGT | GGAAAGGGAA | 1440
| TGAACTTGAT | CTTTGTGGGT | ACTGAGGTTG | GTCCTTGGAG | CAAAACTGGT | GGACTAGGTG | 1500
| ATGTTCTTGG | TGGACTACCA | CCAGCCCTTG | CAGTAAGTCT | TTCTTTCATT | TGGTTACCTA | 1560
| CTCATTCATT | ACTTATTTTG | TTTAGTTAGT | TTCTACTGCA | TCAGTCTTTT | TATCATTTAG | 1620
| GCCCGCGGAC | AGCGGGTAAT | GACAATATCC | CCCGTTATG | ACCAATACAA | AGATGCTTGG | 1680
| GATACTGGCG | TTGCGGTTGA | GGTACATCTT | CCTATATTGA | TACGGTACAA | TATTGTTCTC | 1740
| TTACATTTCC | TGATTCAAGA | ATGTGATCAT | CTGCAGGTCA | AAGTTGGAGA | CAGCATTGAA | 1800
| ATTGTTCGTT | TCTTTCACTG | CTATAAACGT | GGGGTTGATC | GTGTTTTGT | TGACCACCCA | 1860
| ATGTTCTTGG | AGAAAGTAAG | CATATTATGA | TTATGAATCC | GTCCTGAGGG | ATACGCAGAA | 1920
| CAGGTCATTT | TGAGTATCTT | TTAACTCTAC | TGGTGCTTTT | ACTCTTTTAA | GGTTTGGGGC | 1980
| AAAACTGGTT | CAAAAATCTA | TGGCCCCAAA | GCTGGACTAG | ATTATCTGGA | CAATGAACTT | 2040
| AGGTTCAGCT | TGTTGTGTCA | AGTAAGTTAG | TTACTCTTGA | TTTTTATGTG | GCATTTACT | 2100
| CTTTTGTCTT | TAATCGTTTT | TTTAACCTTG | TTTTCTCAGG | CAGCCCTAGA | GGCACCTAAA | 2160
| GTTTTGAATT | TGAACAGTAG | CAACTACTTC | TCAGGACCAT | ATGGTAATTA | ACACATCCTA | 2220
| GTTTCAGAAA | ACTCCTTACT | ATATCATTGT | AGGTAATCAT | CTTTATTTTG | CCTATTCCTG | 2280
| CAGGAGAGGA | TGTTCTCTTC | ATTGCCAATG | ATTGGCACAC | AGCTCTCATT | CCTTGCTACT | 2340
| TGAAGTCAAT | GTACCAGTCC | AGAGGAATCT | ACTTGAATGC | CAAGGTAAAA | TTTCTTTGTA | 2400
| TTCACTCGAT | TGCACGTTAC | CCTGCAAATC | AGTAAGGTTG | TATTAATATA | TGATAAATTT | 2460
| CACATTGCCT | CCAGGTTGCT | TTCTGCATCC | ATAACATTGC | CTACCAAGGT | CGATTTTCTT | 2520
| TCTCTGACTT | CCCTCTTCTC | AATCTTCCTG | ATGAATTCAG | GGGTTCTTTT | GATTTCATTG | 2580
| ATGGGTATGT | ATTTATGCTT | GAAATCAGAC | CTCCAACTTT | TGAAGCTCTT | TTGATGCTAG | 2640
| TAAATTGAGT | TTTTAAAATT | TTGCAGATAT | GAGAAGCCTG | TTAAGGGTAG | GAAAATCAAC | 2700
| TGGATGAAGG | CTGGGATATT | AGAATCACAT | AGGGTGGTTA | CAGTGAGCCC | ATACTATGCC | 2760
| CAAGAACTTG | TCTCTGCTGT | TGACAAGGGA | GTTGAATTGG | ACAGTGTCCT | TCGTAAGACT | 2820
| TGCATAACTG | GGATTGTGAA | TGGCATGGAT | ACACAAGAGT | GGAACCCAGC | GACTGACAAA | 2880
| TACACAGATG | TCAAATACGA | TATAACCACT | GTAAGATAAG | ATTTTTCCGA | CTCCAGTATA | 2940
| TACTAAATTA | TTTTGTATGT | TTATGAAATT | AAAGAGTTCT | TGCTAATCAA | AATCTCTATA | 3000
| CAGGTCATGG | ACGCAAAACC | TTTACTAAAG | GAGGCTCTTC | AAGCAGCAGT | TGGCTTGCCT | 3060
| GTTGACAAGA | AGATCCCTTT | GATTGGCTTC | ATCGGCAGAC | TTGAGGAGCA | GAAAGGTTCA | 3120
| GATATTCTTG | TTGCTGCAAT | TCACAAGTTC | ATCGGATTGG | ATGTTCAAAT | TGTAGTCCTT | 3180
| GTAAGTACCA | AATGGACTCA | TGGTATCTCT | CTTGTTGAGT | TTACTTGTGC | CGAAACTGAA | 3240
| ATTGACCTGC | TACTCATCCT | ATGCATCAGG | GAACTGGCAA | AAAGGATTTT | GAGCAGGAGA | 3300
| TTGAACAGCT | CGAAGTGTTG | TACCCTAACA | AAGCTAAAGG | AGTGGCAAAA | TTCAATGTCC | 3360
| CTTTGGCTCA | CATGATCACT | GCTGGTGCTG | ATTTTATGTT | GGTTCCAAGC | AGATTTGAAC | 3420
| CTTGTGGTCT | CATTCAGTTA | CATGCTATGC | GATATGGAAC | AGTAAGAACC | AGAAGAGCTT | 3480
| GTACCTTTTT | ACTGAGTTTT | TAAAAAAGA | ATCATAAGAC | CTTGTTTTCC | ATCTAAAGTT | 3540
| TAATAACCAA | CTAAATGTTA | CTGCAGCAAG | CTTTTCATTT | CTGAAAATTG | GTTATCTGAT | 3600
| TTTAACGTAA | TCACATGTGA | GTCAGGTACC | AATCTGTGCA | TCGACTGGTG | GACTTGTTGA | 3660

-continued

| | | | | | |
|---|---|---|---|---|---|
| CACTGTGAAA | GAAGGCTATA | CTGGATTCCA | TATGGGAGCC | TTCAATGTTG | AAGTATGTGA | 3720
| TTTTACATCA | ATTGTGTACT | TGTACATGGT | CCATTCTCGT | CTTGATATAC | CCCTTGTTGC | 3780
| ATAAACATTA | ACTTATTGCT | TCTTGAATTT | GGTTAGTGCG | ATGTTGTTGA | CCCAGCTGAT | 3840
| GTGCTTAAGA | TAGTAACAAC | AGTTGCTAGA | GCTCTTGCAG | TCTATGGCAC | CCTCGCATTT | 3900
| GCTGAGATGA | TAAAAAATTG | CATGTCAGAG | GAGCTCTCCT | GGAAGGTAAG | TGTGAATTTG | 3960
| ATAATTTGCG | TAGGTACTTC | AGTTTGTTGT | TCTCGTCAGC | ACTGATGGAT | TCCAACTGGT | 4020
| GTTCTTGCAG | GAACCTGCCA | AGAAATGGGA | GACATTGCTA | TTGGGCTTAG | GAGCTTCTGG | 4080
| CAGTGAACCC | GGTGTTGAAG | GGGAAGAAAT | CGCTCCACTT | GCCAAGGAAA | ATGTAGCCAC | 4140
| TCCTTAAATG | AGCTTTGGTT | ATCCTTGTTT | CAACAATAAG | ATCATTAAGC | AAACGTATTT | 4200
| ACTAGCGAAC | TATGTAGAAC | CCTATTATGG | GGTCTCAATC | ATCTACAAAA | TGATTGGTTT | 4260
| TTGCTGGGGA | GCAGCAGCAT | ATAAGGCTGT | AAAATCCTGG | TTAATGTTTT | TGTAGGTAAG | 4320
| GGCTATTTAA | GGTGGTGTGG | ATCAAAGTCA | ATAGAAATA | GTTATTACTA | ACGTTTGCAA | 4380
| CTAAATACTT | AGTAATGTAG | CATAAATAAT | ACTAGAACTA | GTAGCTAATA | TATATGCGTG | 4440
| AATTTGTTGT | ACCTTTTCTT | GCATAATTAT | TTGCAGTACA | TATATAATGA | AAATTACCCA | 4500
| AGGAATCAAT | GTTTCTTGCT | CCGTCCTCCT | TTGATGATTT | TTTACGCAAT | ACAGAGCTAG | 4560
| TGTGTTATGT | TATAAATTTT | GTTTAAAAGA | AGTAATCAAA | TTCAAATTAG | TTGTTTGGTC | 4620
| ATATGAAAGA | AGCTGCCAGG | CTAACTTTGA | GGAGATGGCT | ATTGAATTTC | AAAATGATTA | 4680
| TGTGAAAACA | ATGCAACATC | TATGTCAATC | AACACTTAAA | TTATTGCATT | TAGAAAGATA | 4740
| TTTTTGAGCC | CATGACACAT | TCATTCATAA | AGTAAGGTAG | TATGTATGAT | TGAATGGACT | 4800
| ACAGCTCAAT | CAAAGCATCT | CCTTTACATA | ACGGCACTGT | CTCTTGTCTA | CTACTCTATT | 4860
| GGTAGTAGTA | GTAGTAATTT | TACAATCCAA | ATTGAATAGT | AATAAGATGC | TCTCTATTTA | 4920
| CTAAAGTAGT | AGTATTATTC | TTTCGTTACT | CTAAAGCAAC | AAAA | | 4964

( 2 ) INFORMATION FOR SEQ ID NO:6:

( i ) SEQUENCE CHARACTERISTICS:
        ( A ) LENGTH: 69 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..69
        ( D ) OTHER INFORMATION: /note= "Amino acid sequence encoded
            by nucleotides 1-207 of SEQ ID NO. 2."

( x i ) SEQUENCE DESCRIPTION: SEQ ID NO:6:

```
Asn Lys Leu Asp Gly Leu Gln Ser Thr Thr Asn Thr Lys Val Thr Pro
 1               5                  10                  15

Lys Met Ala Ser Arg Thr Glu Thr Lys Arg Pro Gly Cys Ser Ala Thr
            20                  25                  30

Ile Val Cys Gly Lys Gly Met Asn Leu Ile Phe Val Gly Thr Glu Val
        35                  40                  45

Gly Pro Trp Ser Lys Thr Gly Gly Leu Gly Asp Val Leu Gly Gly Leu
    50                  55                  60

Pro Pro Ala Leu Ala
65
```

( 2 ) INFORMATION FOR SEQ ID NO:7:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1..27
    ( D ) OTHER INFORMATION: /note= "Amino acid sequence encoded
        by nucleotides 296-377 of SEQ ID NO. 2."

( x i ) SEQUENCE DESCRIPTION: SEQ ID NO:7:

```
Ala  Arg  Gly  His  Arg  Val  Met  Thr  Ile  Ser  Pro  Arg  Tyr  Asp  Gln  Tyr
1                   5                        10                       15
Lys  Asp  Ala  Trp  Asp  Thr  Gly  Val  Ala  Val  Glu
                20                       25
```

( 2 ) INFORMATION FOR SEQ ID NO:8:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..33
        ( D ) OTHER INFORMATION: /note= "Amino acid sequence encoded
            by nucleotides 452-550 of SEQ ID NO. 2."

( x i ) SEQUENCE DESCRIPTION: SEQ ID NO:8:

```
Val  Lys  Val  Gly  Asp  Ser  Ile  Glu  Ile  Val  Arg  Phe  Phe  His  Cys  Tyr
1                   5                        10                       15
Lys  Arg  Gly  Val  Asp  Arg  Val  Phe  Val  Asp  His  Pro  Met  Phe  Leu  Glu
                20                       25                       30
Lys
```

( 2 ) INFORMATION FOR SEQ ID NO:9:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..30
        ( D ) OTHER INFORMATION: /note= "Amino acid sequence encoded
            by nucleotides 647-736 of SEQ ID NO. 2."

( x i ) SEQUENCE DESCRIPTION: SEQ ID NO:9:

```
Val  Trp  Gly  Lys  Thr  Gly  Ser  Lys  Ile  Tyr  Gly  Pro  Lys  Ala  Gly  Leu
1                   5                        10                       15
Asp  Tyr  Leu  Asp  Asn  Glu  Leu  Arg  Phe  Ser  Leu  Leu  Cys  Gln
                20                       25                       30
```

( 2 ) INFORMATION FOR SEQ ID NO:10:

( i ) SEQUENCE CHARACTERISTICS:
        ( A ) LENGTH: 21 amino acids (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1..21
                (D) OTHER INFORMATION: /note= "Amino acid sequence encoded
                    by nucleotides 815-878 of SEQ ID NO. 2."

(xi) SEQUENCE DESCRIPTION: SEQ ID NO:10:

Ala   Ala   Leu   Glu   Ala   Pro   Lys   Val   Leu   Asn   Leu   Asn   Ser   Ser   Asn   Tyr
    1                       5                             10                            15

Phe   Ser   Gly   Pro   Tyr
                      20

(2) INFORMATION FOR SEQ ID NO:11:

(i) SEQUENCE CHARACTERISTICS:
                (A) LENGTH: 34 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1..34
                (D) OTHER INFORMATION: /note= "Amino acid sequence encoded
                    by nucleotides 878 and 959-1059 of SEQ ID NO. 2."

(xi) SEQUENCE DESCRIPTION: SEQ ID NO:11:

Gly   Glu   Asp   Val   Leu   Phe   Ile   Ala   Asn   Asp   Trp   His   Thr   Ala   Leu   Ile
    1                       5                             10                            15

Pro   Cys   Tyr   Leu   Lys   Ser   Met   Tyr   Gln   Ser   Arg   Gly   Ile   Tyr   Leu   Asn
                      20                            25                            30

Ala   Lys (2) INFORMATION FOR SEQ ID NO:12:

(i) SEQUENCE CHARACTERISTICS:
                (A) LENGTH: 38 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1..38
                (D) OTHER INFORMATION: /note= "Amino acid sequence encoded
                    by nucleotides 1150-1263 of SEQ ID NO 2."

(xi) SEQUENCE DESCRIPTION: SEQ ID NO:12:

Val   Ala   Phe   Cys   Ile   His   Asn   Ile   Ala   Tyr   Gln   Gly   Arg   Phe   Ser   Phe
    1                       5                             10                            15

Ser   Asp   Phe   Pro   Leu   Leu   Asn   Leu   Pro   Asp   Glu   Phe   Arg   Gly   Ser   Phe
                      20                            25                            30

Asp   Phe   Ile   Asp   Gly   Tyr
                      35

(2) INFORMATION FOR SEQ ID NO:13:

(i) SEQUENCE CHARACTERISTICS:
                (A) LENGTH: 79 amino acids (B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION: 1..79
(D) OTHER INFORMATION: /note= "Amino acid sequence encoded by nucleotides 1349-1585 of SEQ ID NO 2."

(x i) SEQUENCE DESCRIPTION: SEQ ID NO:13:

```
Lys Pro Val Lys Gly Arg Lys Ile Asn Trp Met Lys Ala Gly Ile Leu
  1               5                  10                  15
Glu Ser His Arg Val Val Thr Val Ser Pro Tyr Tyr Ala Gln Glu Leu
              20                  25                  30
Val Ser Ala Val Asp Lys Gly Val Glu Leu Asp Ser Val Leu Arg Lys
          35                  40                  45
Thr Cys Ile Thr Gly Ile Val Asn Gly Met Asp Thr Gln Glu Trp Asn
      50                  55                  60
Pro Ala Thr Asp Lys Tyr Thr Asp Val Lys Tyr Asp Ile Thr Thr
 65                  70                  75
```

(2) INFORMATION FOR SEQ ID NO:14:

(i) SEQUENCE CHARACTERISTICS:
(A) LENGTH: 59 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION: 1..59
(D) OTHER INFORMATION: /note= "Amino acid sequence encoded by nucleotides 1676-1855 of SEQ ID NO 2."

(x i) SEQUENCE DESCRIPTION: SEQ ID NO:14:

```
Val Met Asp Ala Lys Pro Leu Leu Lys Glu Ala Leu Gln Ala Ala Val
  1               5                  10                  15
Gly Leu Pro Val Asp Lys Lys Ile Pro Leu Ile Gly Phe Ile Gly Arg
              20                  25                  30
Leu Glu Glu Gln Lys Gly Ser Asp Ile Leu Ala Val Ala Ile His Lys
          35                  40                  45
Phe Ile Gly Leu Asp Val Gln Ile Val Val Leu
      50                  55
```

(2) INFORMATION FOR SEQ ID NO:15:

(i) SEQUENCE CHARACTERISTICS:
(A) LENGTH: 64 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION: 1..64
(D) OTHER INFORMATION: /note= "Amino acid sequence encoded by nucleotides 1945-2136 of SEQ ID NO 2."

(x i) SEQUENCE DESCRIPTION: SEQ ID NO:15:

```
Gly Thr Gly Lys Lys Glu Phe Glu Gln Glu Ile Glu Gln Leu Glu Val
```

```
            1               5                       10                          15

Leu  Tyr  Pro  Asn  Lys  Ala  Lys  Gly  Val  Ala  Lys  Phe  Asn  Val  Pro  Leu
                        20                      25                      30

Ala  His  Met  Ile  Thr  Ala  Gly  Ala  Asp  Phe  Met  Leu  Val  Pro  Ser  Arg
                   35                      40                      45

Phe  Glu  Pro  Cys  Gly  Leu  Ile  Gln  Leu  His  Ala  Met  Arg  Tyr  Gly  Thr
              50                      55                      60
```

( 2 ) INFORMATION FOR SEQ ID NO:16:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..29
        ( D ) OTHER INFORMATION: /note= "Amino acid sequence encoded
            by nucleotides 2301-2386 of SEQ ID NO 2."

( x i ) SEQUENCE DESCRIPTION: SEQ ID NO:16:

```
        Val  Pro  Ile  Cys  Ala  Ser  Thr  Gly  Gly  Leu  Val  Asp  Thr  Val  Lys  Glu
         1               5                       10                          15

Gly  Tyr  Thr  Gly  Phe  His  Met  Gly  Ala  Phe  Asn  Val  Glu
                        20                      25
```

( 2 ) INFORMATION FOR SEQ ID NO:17:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..19
        ( D ) OTHER INFORMATION: /note= "Amino acid sequence encoded
            by nucleotides 2492-2459 of SEQ ID NO 2."

( x i ) SEQUENCE DESCRIPTION: SEQ ID NO:17:

```
        Cys  Asp  Val  Val  Asp  Pro  Ala  Asp  Val  Leu  Lys  Ile  Val  Thr  Thr  Val
         1               5                       10                          15

Ala  Arg  Ala
```

( 2 ) INFORMATION FOR SEQ ID NO:18:

( i ) SEQUENCE CHARACTERISTICS:
        ( A ) LENGTH: 111 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..111
        ( D ) OTHER INFORMATION: /note= "Amino acid sequence encoded
            by nucleotides 1200-1532 of SEQ ID NO 5."

( x i ) SEQUENCE DESCRIPTION: SEQ ID NO:18:

```
        Met  Ala  Ser  Ile  Thr  Ala  Ser  His  His  Phe  Val  Ser  Arg  Ser  Gln  Thr
```

|   | 1 |   |   |   | 5 |   |   |   |   | 10 |   |   |   |   | 15 |
|---|---|---|---|---|---|---|---|---|---|----|---|---|---|---|----|
|   | Ser | Leu | Asp | Thr | Lys | Ser | Thr | Leu | Ser | Gln | Ile | Gly | Leu | Arg | Asn | His |
|   |   |   |   | 20 |   |   |   |   | 25 |   |   |   |   | 30 |   |
|   | Thr | Leu | Thr | His | Asn | Gly | Leu | Arg | Ala | Val | Asn | Lys | Leu | Asp | Gly | Leu |
|   |   |   | 35 |   |   |   | 40 |   |   |   |   | 45 |   |   |   |
|   | Gln | Ser | Thr | Thr | Asn | Thr | Lys | Val | Thr | Pro | Lys | Met | Ala | Ser | Arg | Thr |
|   | 50 |   |   |   |   | 55 |   |   |   |   | 60 |   |   |   |   |
|   | Glu | Thr | Lys | Arg | Pro | Gly | Cys | Ser | Ala | Thr | Ile | Val | Cys | Gly | Lys | Gly |
|   | 65 |   |   |   |   | 70 |   |   |   |   | 75 |   |   |   |   | 80 |
|   | Met | Asn | Leu | Ile | Phe | Val | Gly | Thr | Glu | Val | Gly | Pro | Trp | Ser | Lys | Thr |
|   |   |   |   |   | 85 |   |   |   |   | 90 |   |   |   |   | 95 |   |
|   | Gly | Gly | Leu | Gly | Asp | Val | Leu | Gly | Gly | Leu | Pro | Pro | Ala | Leu | Ala |   |
|   |   |   |   | 100 |   |   |   |   | 105 |   |   |   |   | 110 |   |   |

( 2 ) INFORMATION FOR SEQ ID NO:19:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..43
        ( D ) OTHER INFORMATION: /note= "Amino acid sequence encoded
            by nucleotides 3817-3945 of SEQ ID NO. 5."

( x i ) SEQUENCE DESCRIPTION: SEQ ID NO:19:

| Cys | Asp | Val | Val | Asp | Pro | Ala | Asp | Val | Leu | Lys | Ile | Val | Thr | Thr | Val |
|---|---|---|---|---|---|---|---|---|---|---|---|---|---|---|---|
| 1 |   |   |   | 5 |   |   |   |   | 10 |   |   |   |   | 15 |   |
| Ala | Arg | Ala | Leu | Ala | Val | Tyr | Gly | Thr | Leu | Ala | Phe | Ala | Glu | Met | Ile |
|   |   |   | 20 |   |   |   |   | 25 |   |   |   |   | 30 |   |   |
| Lys | Asn | Cys | Met | Ser | Glu | Glu | Leu | Ser | Trp | Lys |   |   |   |   |   |
|   |   | 35 |   |   |   |   | 40 |   |   |   |   |   |   |   |   |

( 2 ) INFORMATION FOR SEQ ID NO:20:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..38
        ( D ) OTHER INFORMATION: /note= "Amino acid sequence encoded
            by nucleotides 4031-4144 of SEQ ID NO. 5."

( x i ) SEQUENCE DESCRIPTION: SEQ ID NO:20:

| Glu | Pro | Ala | Lys | Lys | Trp | Glu | Thr | Leu | Leu | Leu | Gly | Leu | Gly | Ala | Ser |
|---|---|---|---|---|---|---|---|---|---|---|---|---|---|---|---|
| 1 |   |   |   | 5 |   |   |   |   | 10 |   |   |   |   | 15 |   |
| Gly | Ser | Glu | Pro | Gly | Val | Glu | Gly | Glu | Glu | Ile | Ala | Pro | Leu | Ala | Lys |
|   |   |   | 20 |   |   |   |   | 25 |   |   |   |   | 30 |   |   |
| Glu | Asn | Val | Ala | Thr | Pro |   |   |   |   |   |   |   |   |   |   |
|   |   |   | 35 |   |   |   |   |   |   |   |   |   |   |   |   |

( 2 ) INFORMATION FOR SEQ ID NO:21:

( i ) SEQUENCE CHARACTERISTICS:

-continued (A) LENGTH: 17 base pairs
      (B) TYPE: nucleic acid
      (C) STRANDEDNESS: single
      (D) TOPOLOGY: linear (ii) MOLECULE TYPE: RNA (ix) FEATURE:
      (A) NAME/KEY: misc_RNA
      (B) LOCATION: 1
      (D) OTHER INFORMATION: /note= "Nucleotide 1 is a 7-methyl guanine added by 5'-5'linkage as an RNA cap."

(xi) SEQUENCE DESCRIPTION: SEQ ID NO:21:

GAUGGCAAGA AAAAAA                                                                    1 7